United States Patent [19]

Perun et al.

[11] 4,087,528

[45] May 2, 1978

[54] 2,4-DIAMINO-5-BENZYLPYRIMIDINES

[75] Inventors: Thomas John Perun, Libertyville; Ronald Robert Rasmussen; Bruce Wayne Horrom, both of Waukegan, all of Ill.

[73] Assignee: Abbott Laboratories, North Chicago, Ill.

[21] Appl. No.: 735,301

[22] Filed: Oct. 26, 1976

Related U.S. Application Data

[62] Division of Ser. No. 601,118, Jul. 31, 1975, Pat. No. 4,008,236.

[51] Int. Cl.$^2$ .................. A61K 31/305; C07D 239/48
[52] U.S. Cl. .................................................. 424/251
[58] Field of Search ................ 260/256.4 N; 424/251

[56] References Cited

U.S. PATENT DOCUMENTS 3,849,407  11/1974  Cresswell et al. ............ 260/256.4 N

*Primary Examiner*—Donald G. Daus
*Assistant Examiner*—James H. Turnipseed
*Attorney, Agent, or Firm*—Paul D. Burgauer; Robert L. Niblack

[57] ABSTRACT

This invention provides 2,4-diamino-5-benzylpyrimidines represented by the formula

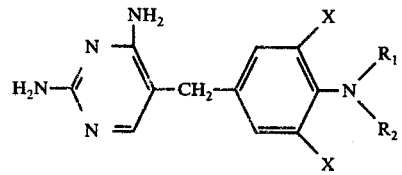

wherein $R_1$ is H or loweralkyl; $R_2$ is H, loweralkyl or $R_3CO-$ wherein $R_3$ is H, alkyl, or cycloalkyl-loweralkyl; and X is a halogen; and the acid addition salts thereof.

These pyrimidine compounds are useful as antibacterial agents, and as potentiators of the anti-bacterial activity of sulfonamides.

8 Claims, No Drawings

2,4-DIAMINO-5-BENZYLPYRIMIDINES

This is a division of application Ser. No. 601,118, filed July 31, 1975 now U.S. Pat. No. 4,008,236 issued Feb. 15, 1977.

DETAILED DESCRIPTION OF THE INVENTION

The invention relates to 2,4-diamino-5-benzylpyrimidines characterized by formula (I):

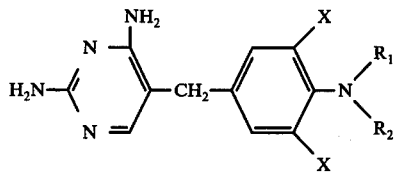

wherein $R_1$ is H or loweralkyl; $R_2$ is H, loweralkyl or $R_3CO$— wherein $R_3$ is H, alkyl, or cycloalkyl-loweralkyl; and X is a halogen; and the acid addition salts thereof.

The term "alkyl" as used herein refers to both straight and branched chain alkyl radicals having 1 to 8 carbon atoms and which include methyl, ethyl, n-butyl, n-pentyl, iso-pentyl, hexyl and the like.

As used herein, the term "loweralkyl-alkyl" means saturated monovalent aliphatic radicals including straight and branched chain radicals of from 1 to 6 carbon atoms, as illustrated by, but not limited to, methyl, ethyl, propyl, iso-propyl, butyl, sec-butyl, amyl, hexyl, and the like.

As used herein, the term "cycloalkyl" means cyclic, saturated, aliphatic radicals of from 3 to 8 carbon atoms, as illustrated by, but not limited to, cyclopropyl, cyclobutyl, 2-methyl-cyclobutyl, cyclohexyl, 4-methylcyclohexyl, cyclooctyl and the like.

The term "halogen" includes chlorine, fluorine, bromine and iodine.

The compounds of this invention exhibit antibacterial activity and are quite useful as a means of removing disease causing bacteria from living organisms.

The compounds of this invention are also useful in potentiating the antibacterial effect of sulfonamides such as sulfadiazine, sulfamethoxazole, sulfamethazine, and sulfamerazine. The combination of these compounds with sulfonamides may increase the antibacterial activity of the sulfa drug by as much as 30-fold. The ratio of compound:sulfonamide in these mixtures may vary over a wide range. For example, the ratio may vary from 1:1 to 1:20. These mixtures may be formulated in dosage forms convenient for administration to patients.

The present compounds may be made according to the following general process scheme:

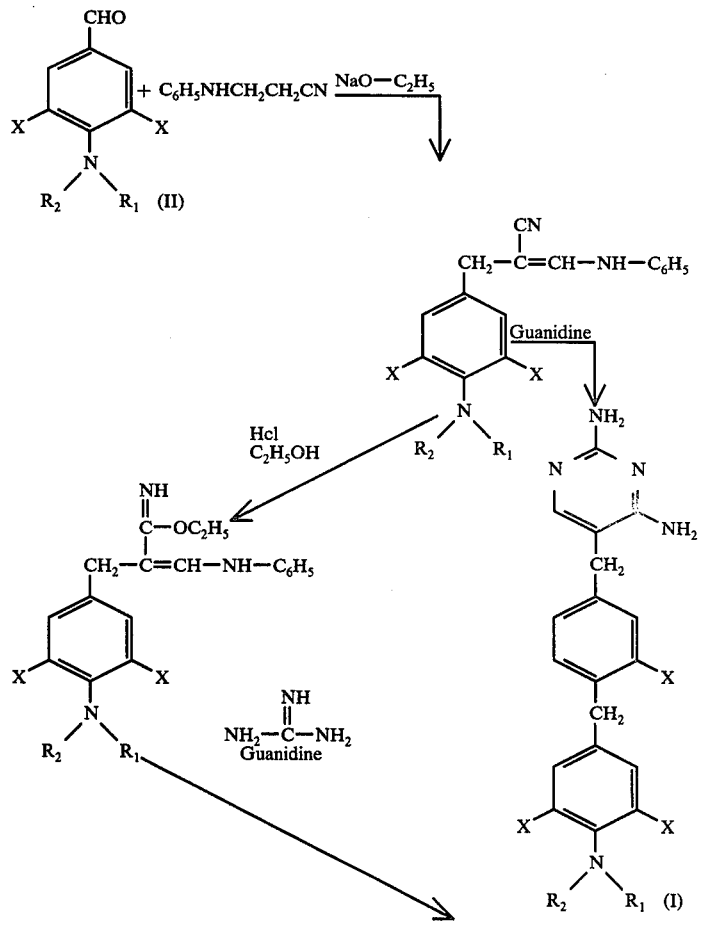

wherein $R_1$ is H or loweralkyl; $R_2$ is H, loweralkyl or $R_3CO$— wherein $R_3$ is H, alkyl, cycloalkyl, loweralkyl; and X is a halogen.

The above process is carried out by first treating an aldehyde of Formula II with 3-anilinopropionitrile in the presence of an alkali metal lower alkoxide. The alkali metal alkoxide is preferably sodium methoxide or sodium ethoxide. The reaction temperature is determined by the temperature of the refluxing solvent which is preferably methanol or ethanol. The resulting substituted acrylonitrile is usually not isolated but instead is treated in situ with guanidine to give the pyrimidine of Formula I. Alternatively, the substituted acrylonitrile can be treated with anhydrous ethanolic hydrochloride to give an imidate ester which then affords the pyrimidine of Formula I after treatment with guanidine. This modified procedure affords somewhat better yields and purer products than the unmodified procedure.

The aldehydes of formula II are prepared according to the scheme below:

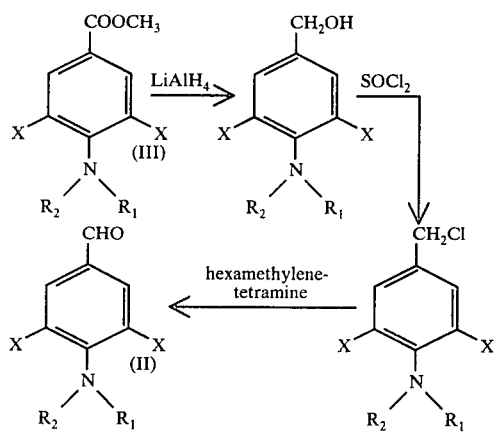

wherein $R_1$, $R_2$, and X are as defined above.

The intermediates such as the benzoic acid methyl ester represented by formula III may be prepared by the method described in U.S. Pat. No. 3,801,636. These intermediates are useful in the preparation of the desired pyrimidine compounds.

Some of the compounds produced by the general process scheme, illustrated above, which come within the scope of Formula (I) are:

2,4-Diamino-5-(4-amino-3,5-dichlorobenzyl)pyrimidine of the formula

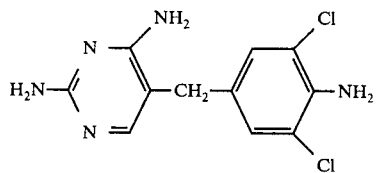

2,4-Diamino-5-(3,5-dichloro-4-methylaminobenzyl)-pyrimidine of the formula

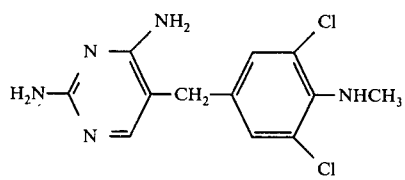

2,4-Diamino-5-(3,5-dichloro-4-ethylaminobenzyl)-pyrimidine of the formula

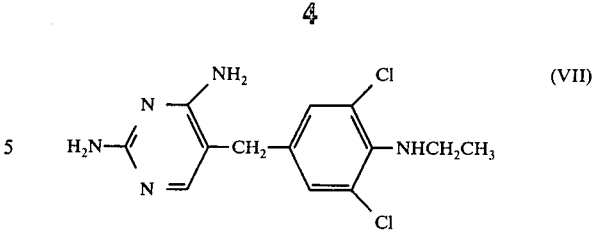

2,4-Diamino-5-(3,5-dichloro-4-dimethylaminobenzyl)pyrimidine of the formula

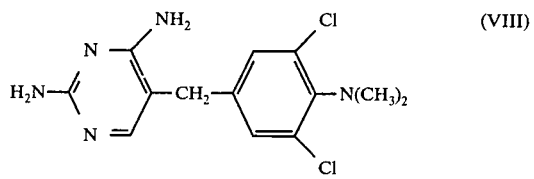

2,4-Diamino-5-(4-acetamido-3,5-dichlorobenzyl)-pyrimidine of the formula

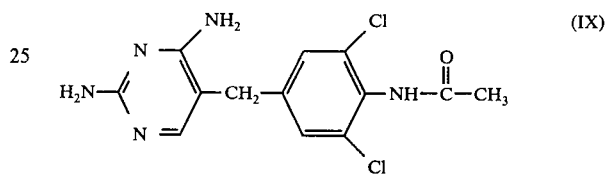

The following examples will serve to further illustrate the preparation of the present compounds and the advantages of the present invention.

EXAMPLE I
2,4-Diamino-5-(4-Amino-3,5-Dichlorobenzyl)Pyrimidine

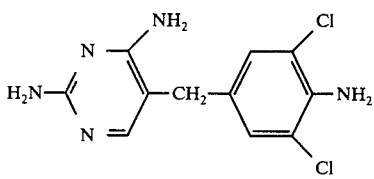

A solution of sodium ethoxide in ethanol was prepared by dissolving 0.58 g. (0.025 mole) of sodium in 250 ml. of absolute ethanol. To this solution was added 15.4 g. (0.105 mole) of 3-anilinopropionitrile followed by 16.2 g. (0.085 mole) of 4-amino-3,5-dichlorobenzaldehyde. This mixture was heated under reflux for 8 hours. The imidate ester was formed by first cooling the above mixture to 10° and then adding 0.7 ml. of 0.4 N ethanolic-HCl. Formation was complete after stirring for 1 hour at 10° C. Guanidine free base, prepared by adding 22.9 g. (0.24 mole) of guanidine hydrochloride to 5.52 g. (0.24 mole) of sodium in 90 ml. of absolute ethanol, was added to the mixture containing the imidate ester. After stirring and heating under reflux for 5 hours, the sodium chloride was removed by filtration and the filtrate concentrated in vacuo until its volume was diminished by one-half. Cooling induced the product to precipitate. Crystallization from isopropanol afforded 3.6 g. of material having a melting point of 241° C.

Analysis Calcd. for $C_{11}H_{11}Cl_2N_5$: C, 46.49; H, 3.90; N, 24.65 Found: C, 42.41; H, 3.42; N, 24.35

In Table 1, the physical data of other compounds produced by the method described above, are shown. The compounds, as identified, are those represented respectively by formulas VI and VIII:

TABLE 1

| Compound | M.P. | Formula | Theory C | Theory H | Theory N | Found C | Found H | Found N |
|---|---|---|---|---|---|---|---|---|
| VI | 202–203° C. | $C_{12}H_{13}Cl_2N_5$ | 48.5 | 3.3 | 23.5 | 48.7 | 4.3 | 23.5 |
| VIII | 193–194° C. | $C_{13}H_{15}Cl_2N_5$ | 50.0 | 4.8 | 22.4 | 50.1 | 4.7 | 22.3 |

These compounds are useful as antibacterial agents.

EXAMPLE II 2,4-Diamino-5-(3,5-Dichloro-4-Ethylaminobenzyl)-Pyrimidine

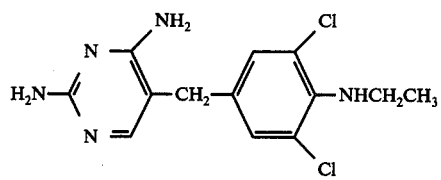

A solution of sodium ethoxide in ethanol was prepared by dissolving 1.15 g. (0.05 mole) of sodium in 500 ml. of absolute ethanol. To this solution was added 30.7 g. (0.209 mole) of 3-anilinopropionitrile followed by 36.4 g. (0.167 mole) of 3,5-dichloro-4-ethylaminobenzaldehyde. This mixture was heated under reflux for 8 hours. To this was added guanidine free base, prepared by adding 45.8 g. (0.48 mole) of guanidine hydrochloride to 11.04 g. (0.48 mole) of sodium in 100 ml. of absolute ethanol. The total mixture was stirred and heated under reflux for 5 hours and then cooled to room temperature. The sodium chloride was removed by filtration and the filtrate concentrated in vacuo until its volume was diminished by one-half. Cooling induced the product to precipitate. Crystallization from isopropanol offered 4.8 g. of material having a melting point of 201°–202° C.

Analysis Calcd. for: $C_{13}H_{15}Cl_2N_5$: C, 50.01; H, 4.84; N, 22.43 Found: C, 49.73; H, 4.87; N, 22.50

EXAMPLE III 2,4-Diamino-5-(4-Acetamido-3,5-Dichlorobenzyl)-Pyrimidine

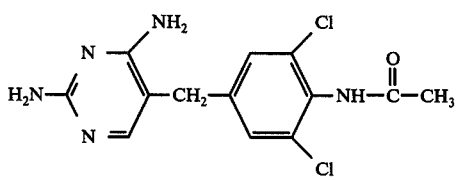

A solution of sodium ethoxide in ethanol was prepared by dissolving 1.15 g. (0.05 mole) of sodium in 500 ml. of absolute ethanol. To this mixture was added 30.7 g. (0.209 mole) of 3-anilinopropionitrile followed by 38.8 g. (0.167 mole) of 4-acetamido-3,5-dichloro-benzaldehyde. This mixture was heated under reflux for 8 hours. Guanidine free base, prepared by adding 45.8 g. (0.48 mole) of guanidine hydrochloride to 11.04 g. (0.48 mole) of sodium in 100 ml. of absolute ethanol, was added to the mixture above. The combined reaction mixture was stirred and heated under reflux for 5 hours and then cooled to room temperature. The sodium chloride was removed by filtration and the filtrate concentrated in vacuo until its volume was diminished by one-half. Cooling induced an oil to form. The oil was triturated with $CH_2Cl_2$ and the $CH_2Cl_2$ was then evaporated in vacuo leaving a solid. Crystallization of the solid from ethanol afforded 3.1 g. of material having a melting point of 251°–253° C.

Analysis Calcd. for $C_{13}H_{13}Cl_2N_5O$: C, 47.87; H, 4.02; N, 21.47 Found: C, 48.05; H, 3.89; N, 21.37

EXAMPLE IV

Several tests have been made to determine the activity of the present pyrimidine compounds as antibacterial agents. The tests have included the following compounds:

(VII) 2,4-Diamino-5-(3,5-dichloro-4-ethylaminobenzyl)pyrimidine;
(VI) 2,4-Diamino-5-(3,5-dichloro-4-methylaminobenzyl)pyrimidine;
(VIII) 2,4-Diamino-5-(3,5-dichloro-4-dimethylaminobenzyl)pyrimidine;
(V) 2,4-Diamino-5-(4-amino-3,5-dichlorobenzyl)pyrimidine.

Test 1

The four compounds, i.e., compounds V, VI, VII, VIII, were tested against a series of strains including:

*Escherichia coli* Juhl and *Escherichia coli* 3100. The method used was a two-fold tube dilution test in 5 ml. amounts of minimal medium. The inoculum was 0.1 ml. of a 1:1T dilution of a 24 hour broth culture. The test was incubated at 37° C. for 18 hours. The results of the test are provided in Table 2 below.

Table 2

| | In Vitro Antimicrobial Activity Minimum Inhibitory Concentration (Mcg./Ml.) Compounds | | | |
|---|---|---|---|---|
| Organism | VII | VI | VIII | V |
| *Escherichia coli* Juhl | 3.1 | 6.2 | 6.2 | 0.78 |
| *Escherichia coli* 3100 | 6.2 | 3.1 | 6.2 | 0.39 |
| *Enterobacter aerogenes* 13048 | 25 | 3.1 | 3.1 | 1.56 |
| *Proteus mirabilis* Finland #9 | 50 | 12.5 | 25 | 25 |
| *Salmonella typhimurium* Ed 9 | 12.5 | 3.1 | 6.2 | 3.1 |
| *Klebsiella pneumoniae* 8045 | 12.5 | 6.2 | 6.2 | 1.56 |

Test 2

A similar test was made on other strains with the compounds (V, VI, VII and VIII) in 5 ml. amounts of Mueller Hinton Medium. The results of this test are provided in Table 3 below:

Table 3

| | Minimum Inhibitory Concentration (Mcg./Ml.) (Mueller Hinton Medium) Compounds | | | |
|---|---|---|---|---|
| Organism | VII | VI | VIII | V |
| *Staphylococcus aureus* 209P | 3.1 | 3.1 | 1.56 | 6.2 |
| *Staphylococcus aureus* Smith | 6.2 | 6.2 | 3.1 | 25 |

Table 3-continued

| | Minimum Inhibitory Concentration (Mcg./Ml.) (Mueller Hinton Medium) Compounds | | | |
|---|---|---|---|---|
| Organism | VII | VI | VIII | V |
| Streptococcus pyogenes C203 | 12.5 | 6.2 | 3.1 | 6.2 |

Test 3

Compounds V – VIII were tested and compared with trimethoprim, as control, against two external strains, (Escherichia coli) a sensitive No. 114 and a No. 114 carrying a resistant (R) factor which mediates the synthesis of an altered dihydrofolate reductase; S. G. R. Amyes and J. T. Smith, Biochem. and Biophys., Res. Comm., 58, 412 (1974).

The method used was a two-fold tube dilution test in 5 ml. amounts of minimal medium. The inoculum was 0.1 ml. of a 1:1T dilution of a 24 hour broth culture. The test was incubated at 37° C. for 18 hours.

The results of the test are shown below in Table 4.

Table 4

In Vitro Antimicrobial Activity vs. Trimethoprim Resistant E. Coli
Minimum Inhibitory Concentration (Mcg./Ml.)

| Compound | E. Coli 114 Sensitive | E. Coli (Resistant) |
|---|---|---|
| Trimethoprim | 0.2 | 3000 |
| VII | 3.1 | 200 |
| VI | 1.56 | >400 |
| VIII | 6.2 | 100 |
| V | 1.56 | 400 |

As shown above, the presence of the resistant (R) factor in E. Coli 114 caused an increase in trimethoprim resistance of several thousand-fold, whereas the increase in resistance to compounds V – VIII is significantly less than this.

Test 4

The potentiation properties of the compounds, i.e., compounds V – VIII in various combinations with sulfa compounds, i.e., sulfonamides (sulfamethoxazole, sulfadiazine, sulfamethazine and sulfamerazine) were tested.

The method was a two-fold tube dilution test using BBL Nutrient broth in 5 ml. amounts. The inoculum was 0.1 ml. of a $10^{-3}$ dilution 24 hour broth culture of Escherichia Coli 3100. The test was incubated at 37° C. for 18 hours.

The results of the test are provided below in Table 5.

Table 5

In Vitro Potentiation of Sulfonamides vs. E. Coli 3100

| Compound | Sulfonamide | Compound/Sulfa Ratio | Potentiation* |
|---|---|---|---|
| VII | Sulfamethoxazole | 1:5 | 3.1 X |
| VII | Sulfamethoxazole | 1:1 | 4.0 X |
| VII | Sulfadiazine | 1:5 | 6.2 X |
| VII | Sulfadiazine | 1:1 | 8.0 X |
| VII | Sulfamethazine | 1:5 | 3.2 X |
| VII | Sulfamethazine | 1:1 | 4.0 X |
| VII | Sulfamerazine | 1:5 | 3.2 X |
| VII | Sulfamerazine | 1:1 | 8.0 X |
| VI | Sulfadiazine | 1:5 | 3.1 X |
| VI | Sulfadiazine | 1:1 | 15.9 X |
| VIII | Sulfadiazine | 1:5 | 1.6 X |
| VIII | Sulfadiazine | 1:1 | 8.0 X |
| V | Sulfadiazine | 1:5 | 3.1 X |

Table 5-continued

In Vitro Potentiation of Sulfonamides vs. E. Coli 3100

| Compound | Sulfonamide | Compound/Sulfa Ratio | Potentiation* |
|---|---|---|---|
| V | Sulfadiazine | 1:1 | 31.0 X |

*The potentiation effect shown is determined by measuring the minimum inhibitory concentration (MIC) of the sulfonamide alone and in combination with the compound at the indicated ratios.

Test 5

Acute Mouse Protection Test

The test bacteria were transferred to Brain Heart Infusion Broth and incubated at 37° C. for 18 hours. Log dilutions of the organism were made in BHI broth and mixed with 3% hog gastric mucin.

Female, Swiss albino mice, 18 – 20 grams, were injected intraperitoneally with 0.75 ml. of inoculum.

The optimum dilution was one in which each mouse received 10 – 10 $LD_{50}$'s of the infecting organism.

The test compound was diluted in such a way that there were 5 drug levels (each level is half as concentrated as the one above) in each test. Ten infected mice were treated with each level of drug. The mice were medicated 1 and 5 hours post-infection.

The mouse mortality was observed for 7 days.

An approximate $CD_{50}$ in mg/kg of the in vivo activity of combinations of a sulfa drug and compounds V – VIII is recorded below in Table 6.

Table 6

In Vivo Activity of Combinations In Acute Mouse Protection Test

| | $CD_{50}$ (Mg./Kg.) | | | |
|---|---|---|---|---|
| Organism | Sulfa Cmpd. VII | Sulfa Cmpd. VI | Sulfa Cmpd. VIII | Sulfa Cmpd. V |
| E. Coli (Juhl) | 175/35 | 150/30 | 225/45 | 225/45 |
| E. Coli (48) | 10/2 | 15/3 | 15/3 | — |
| P. Mirabilis | 150/30 | 300/60 | 400/80 | 150/30 |
| P. Vulgaris | 10/2 | 10/2 | 10/2 | 5 |

Sulfa = Sulfamethoxazole

The data shows that the combinations are effective in curing lethal infections in mice.

We claim:

1. An antibacterial composition containing as the antibacterial components a compound of the formula

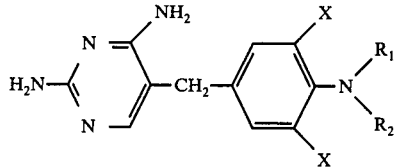

wherein $R_1$ is H or loweralkyl; $R_2$ is H, loweralkyl or $R_3CO$ wherein $R_3$ is H or loweralkyl, and $x$ is a halogen or a pharmaceutically-acceptable acid addition salt thereof; and a sulfonamide selected from the group consisting of sulfadiazine, sulfamethoxazole, sulfamethazine and sulfamerazine, said components being present in a ratio of between 1:1 and 1:20.

2. A composition according to claim 1, wherein said compound is 2,4-diamino-5-(3,5-dichloro-4-ethylaminobenzyl)pyrimidine and said sulfonamide is sulfamethoxazole.

3. A composition according to claim 1, wherein said compound is 2,4-diamino-5-(4-amino-3,5-dichlorobenzyl)pyrimidine and said sulfonamide is sulfadiazine.

4. A composition according to claim 1, wherein said compound is 2,4-diamino-5-(3,5-dichloro-4-methylaminobenzyl)pyrimidine and said sulfonamide is dulfadiazine.

5. A composition according to claim 1, wherein said compound is 2,4-diamino-5-(3,5-dichloro-4-dimethylaminobenzyl)pyrimidine and said sulfonamide is sulfadiazine.

6. A composition according to claim 1, wherein said compound is 2,4-diamino-5-(3,5-dichloro-4-ethylaminobenzyl)pyrimidine and said sulfonamide is sulfamerazine.

7. A composition according to claim 1, wherein said compound is 2,4-diamino-5-(3,5-dichloro-4-ethylaminobenzyl)pyrimidine and said sulfonamide is sulfamethazine.

8. A composition according to claim 1, wherein said compound is 2,4-diamino-5-(3,5-dichloro-4-ethylaminobenzyl)pyrimidine and said sulfonamide is sulfadiazine.

* * * * *

UNITED STATES PATENT AND TRADEMARK OFFICE
CERTIFICATE OF CORRECTION

PATENT NO. : 4,087,528
DATED : May 2, 1978
INVENTOR(S) : T. J. Perun et al.

It is certified that error appears in the above-identified patent and that said Letters Patent are hereby corrected as shown below:

In Column 2, the following partial structure under "Guanidine"

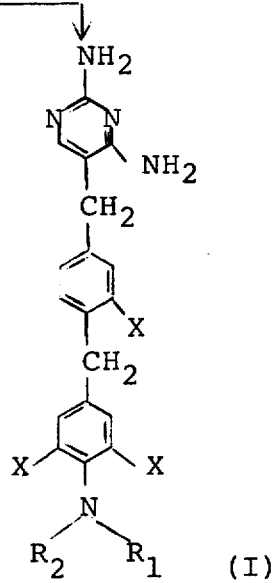

should read:

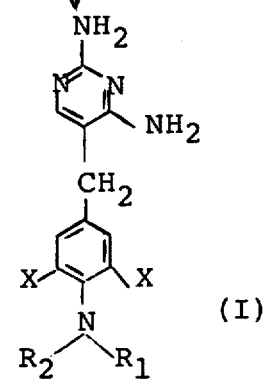

UNITED STATES PATENT AND TRADEMARK OFFICE
CERTIFICATE OF CORRECTION

PATENT NO. : 4,087,528
DATED : May 2, 1978
INVENTOR(S) : T. J. Perun et al.

It is certified that error appears in the above-identified patent and that said Letters Patent are hereby corrected as shown below:

In column 9, Claim 4, delete "dulfadiazine" and substitute therefor -- sulfadiazine --.

Signed and Sealed this

*Twenty-fourth* Day of *October 1978*

[SEAL]

Attest:

RUTH C. MASON
*Attesting Officer*

DONALD W. BANNER
*Commissioner of Patents and Trademarks*